United States Patent
Bhattacharyya et al.

(10) Patent No.: US 10,151,706 B1
(45) Date of Patent: Dec. 11, 2018

(54) INSPECTION FOR SPECIMENS WITH EXTENSIVE DIE TO DIE PROCESS VARIATION

(71) Applicant: KLA-Tencor Corporation, Milpitas, CA (US)

(72) Inventors: Santosh Bhattacharyya, San Jose, CA (US); Hucheng Lee, Cupertino, CA (US); Bjorn Brauer, Beaverton, OR (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/481,421

(22) Filed: Apr. 6, 2017

Related U.S. Application Data

(60) Provisional application No. 62/319,579, filed on Apr. 7, 2016.

(51) Int. Cl.
  *G01N 21/95* (2006.01)
  *G01N 21/88* (2006.01)

(52) U.S. Cl.
  CPC ..... *G01N 21/9503* (2013.01); *G01N 21/8851* (2013.01); *G01N 2021/8887* (2013.01)

(58) Field of Classification Search
  CPC .......... G01N 21/95607; G01N 21/9505; G03F 7/7065; G06T 7/0002; G06T 7/001; G06T 2207/30148; H01J 37/28; H01J 2237/202
  See application file for complete search history.

(56) References Cited

U.S. PATENT DOCUMENTS

| | | | |
|---|---|---|---|
| 6,232,787 B1 * | 5/2001 | Lo | H01J 37/268 250/311 |
| 6,252,412 B1 * | 6/2001 | Talbot | G06T 7/0004 324/754.22 |
| 6,377,898 B1 | 4/2002 | Steffan et al. | |
| 6,509,750 B1 | 1/2003 | Talbot et al. | |
| 6,563,324 B1 | 5/2003 | Nichani | |
| 6,727,512 B2 | 4/2004 | Stokowski et al. | |
| 7,253,645 B2 | 8/2007 | Talbot et al. | |
| 7,474,967 B2 | 1/2009 | Zhong et al. | |
| 7,570,796 B2 | 8/2009 | Zafar et al. | |
| 7,676,077 B2 | 3/2010 | Kulkarni et al. | |
| 7,796,801 B2 | 9/2010 | Kitamura et al. | |
| 7,796,804 B2 | 9/2010 | Bhaskar et al. | |
| 7,924,420 B2 | 4/2011 | Shomrony et al. | |
| 7,965,887 B2 | 6/2011 | Wallack et al. | |
| 8,041,103 B2 | 10/2011 | Kulkarni et al. | |
| 8,126,255 B2 | 2/2012 | Bhaskar et al. | |
| 8,294,094 B1 | 10/2012 | Zhao et al. | |
| 8,415,813 B2 | 4/2013 | Wang et al. | |
| 8,422,761 B2 | 4/2013 | Kitamura et al. | |

(Continued)

*Primary Examiner* — Sang Nguyen
(74) *Attorney, Agent, or Firm* — Ann Marie Mewherter

(57) ABSTRACT

Methods and systems for detecting defects on a specimen are provided. One method includes identifying first and second portions of dies on a specimen as edge dies and center dies, respectively. The method also includes determining first and second inspection methods for the first and second portions, respectively. Parameter(s) of comparisons performed in the first and second inspection methods are different. The method further includes detecting defects in at least one of the edge dies using the first inspection method and detecting defects in at least one of the center dies using the second inspection method.

20 Claims, 5 Drawing Sheets

(56) References Cited

U.S. PATENT DOCUMENTS

| | | | |
|---|---|---|---|
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,699,784 B2 | 4/2014 | Langmatz et al. | |
| 8,716,662 B1 | 5/2014 | MacDonald et al. | |
| 8,937,281 B2 | 1/2015 | Zhao et al. | |
| 9,070,622 B2 | 6/2015 | Ke et al. | |
| 9,222,895 B2 | 12/2015 | Duffy et al. | |
| 9,262,821 B2 | 2/2016 | Shifrin et al. | |
| 2002/0166964 A1 | 11/2002 | Talbot et al. | |
| 2003/0216010 A1* | 11/2003 | Atlas | H01L 21/78 |
| | | | 438/462 |
| 2005/0200841 A1* | 9/2005 | Talbot | G06T 7/0004 |
| | | | 356/237.4 |
| 2006/0291714 A1* | 12/2006 | Wu | G01N 21/95607 |
| | | | 382/149 |
| 2007/0230770 A1* | 10/2007 | Kulkarni | G06F 17/5045 |
| | | | 382/149 |
| 2007/0288219 A1 | 12/2007 | Zafar et al. | |
| 2014/0153814 A1* | 6/2014 | Lin | G06T 7/001 |
| | | | 382/149 |
| 2015/0324964 A1* | 11/2015 | Shifrin | G06T 7/001 |
| | | | 382/151 |

\* cited by examiner

INSPECTION FOR SPECIMENS WITH EXTENSIVE DIE TO DIE PROCESS VARIATION

BACKGROUND OF THE INVENTION

1. Field of the Invention

This invention generally relates to methods and systems for inspecting specimens with extensive die to die process variation.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate all of the defects may be difficult and expensive.

In current wafer manufacturing processes, noise levels are typically not uniform across die rows, i.e., some dies are noisier than others in the same die row. Typically, edge dies (i.e., dies located closest to the edges of the wafers) are noisier than inner dies (i.e., dies located farther from the edges of the wafer than other dies and/or dies not located adjacent to an edge of the wafer). Edge dies also typically have a greater number of defects (e.g., a higher defect density) than center dies because it is more difficult to optimize processes for edge dies and center dies rather than just center dies. In order to compensate for higher noise level detection and defect detection in the edge dies, the inspection tool may inspect edge dies with a different defect detection threshold than the inner dies to catch a similar number of defects from edge and inner dies. In this manner, the edge die threshold is higher than the inner die threshold.

In addition, current inspection tends to compare edge dies to inner, non-edge dies when adjacent edge dies are not available. Such comparison often produces spurious defects. These are the inefficiencies in the current wafer manufacturing process.

Currently used wafer inspection methods have, therefore, a number of disadvantages. For example, as described further above, the noise characteristics of edge dies and inner dies are different. Hence, a comparison between these two types of dies produces additional spurious noise compared to the case when edge dies are compared against other edge dies. Thus, the current comparison of edge dies to non-edge dies produces additional nuisance defects for the edge dies.

Accordingly, it would be advantageous to develop systems and/or methods for detecting defects on a specimen such as a wafer, which has relatively extensive die to die process variation, that do not have one or more of the disadvantages described above.

SUMMARY OF THE INVENTION

The following description of various embodiments is not to be construed in any way as limiting the subject matter of the appended claims.

One embodiment relates to a system configured to detect defects on a specimen. The system includes an inspection subsystem that includes at least an energy source and a detector. The energy source is configured to generate energy that is directed to a specimen. The detector is configured to detect energy from the specimen and to generate output responsive to the detected energy. The system also includes one or more computer subsystems configured for identifying a first portion of dies on the specimen as edge dies based on positions of the dies on the specimen. The computer subsystem(s) are also configured for identifying a second portion of the dies on the specimen as center dies based on the positions of the dies on the specimen. The center dies are located farther from an edge of the specimen than the edge dies.

In addition, the computer subsystem(s) are configured for determining a first inspection method for the first portion of the dies based on the positions of the edge dies on the specimen and a second inspection method for the second portion of the dies based on the positions of the center dies on the specimen. One or more parameters of comparisons of the dies performed in the first inspection method are different than one or more parameters of comparisons of the dies performed in the second inspection method. The computer subsystem(s) are further configured for detecting defects in at least one of the edge dies by performing the first inspection method for the at least one edge die in the first portion. Performing the first inspection method includes performing the comparisons in the first inspection method with the output of the detector for the at least one edge die. The computer subsystem(s) are also configured for detecting defects in at least one of the center dies by performing the second inspection method for the at least one center die in the second portion. Performing the second inspection method includes performing the comparisons in the second inspection method with the output of the detector for the at least one center die. The system may be further configured as described herein.

Another embodiment relates to a computer-implemented method for detecting defects on a specimen. The method includes identifying a first portion of dies on a specimen as edge dies based on positions of the dies on the specimen and identifying a second portion of the dies on the specimen as center dies based on the positions of the dies on the specimen. The center dies are located farther from an edge of the specimen than the edge dies. The method also includes determining a first inspection method for the first portion of the dies based on the positions of the edge dies on the specimen and a second inspection method for the second portion of the dies based on the positions of the center dies on the specimen. One or more parameters of comparisons of the dies performed in the first inspection method are different than one or more parameters of comparisons of the dies performed in the second inspection method.

The method further includes detecting defects in at least one of the edge dies by performing the first inspection method for the at least one edge die in the first portion. Performing the first inspection method includes performing the comparisons in the first inspection method with output of a detector of an inspection subsystem for at least one edge die. The inspection subsystem includes at least an energy source and the detector. The energy source is configured to generate energy that is directed to the specimen, and the detector is configured to detect energy from the specimen and to generate output responsive to the detected energy. In addition, the method includes detecting defects in at least one of the center dies by performing the second inspection method for the at least one center die in the center portion. Performing the second inspection method includes performing the comparisons in the second inspection method with the output of the detector for the at least one center die. Identifying the first portion, identifying the second portion, determining the first and second inspection methods, detecting defects in the at least one edge die, and detecting defects in the at least one center die are performed by one or more computer subsystems coupled to the inspection subsystem.

The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executable on a computer system for performing a computer-implemented method for detecting defects on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

Figure 1:
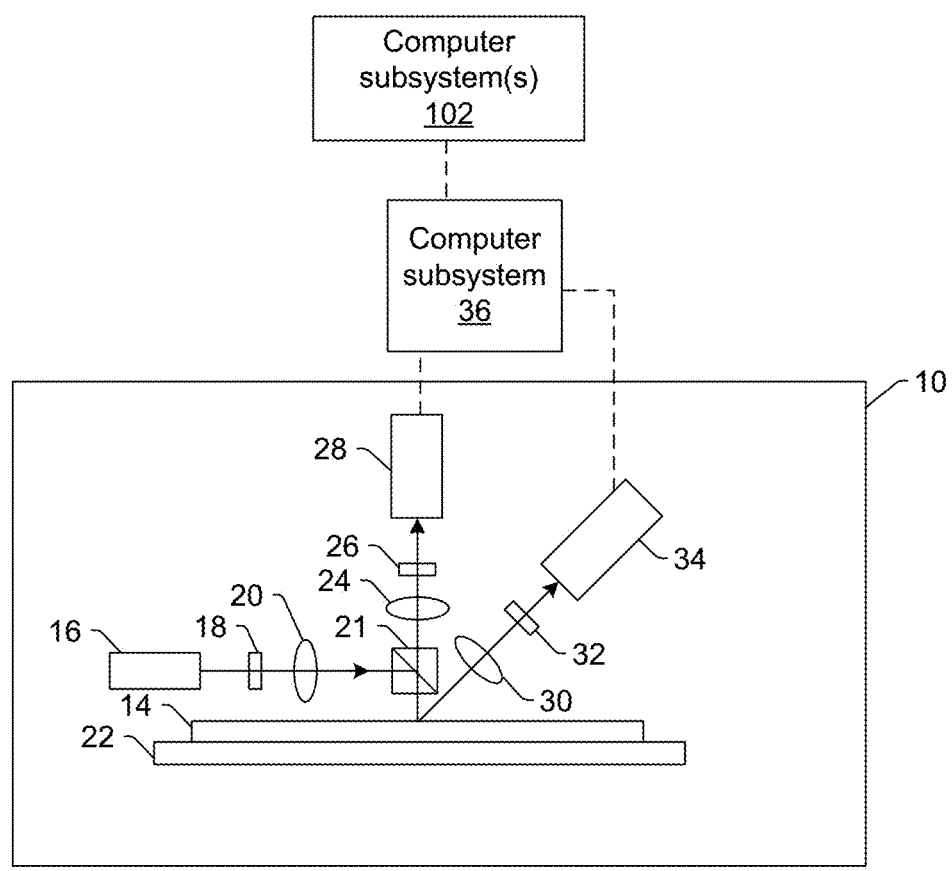
FIGS. 1 and 2 are schematic diagrams illustrating side views of embodiments of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, the design patterns formed on the wafer may not accurately represent the design for the wafer and the wafer inspection system may not be capable of generating images of the design patterns formed on the wafer with sufficient resolution such that the images could be used to determine information about the design for the wafer. Therefore, in general, the design information or design data cannot be generated using a physical wafer. In addition, the "design" and "design data" described herein refers to information and data that is generated by a semiconductor device designer in a design process and is therefore available for use in the embodiments described herein well in advance of printing of the design on any physical wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects on a specimen. The embodiments described herein are particularly suitable for inspecting specimens such as wafers having extensive die to die process variation. The embodiments described herein generally segregate dies in a radial direction so that dies with similar noise characteristics will be inspected together. In this manner, the embodiments described herein are new systems and methods for inspection based on radial position of dies within a die layout on a specimen such as a wafer. In general, the sample plan and swathing strategy of the embodiments described herein is modified so that inner dies are compared against each other and edge dies are compared against other edge dies.

In one embodiment, the specimen includes a wafer. The wafer may include any wafer known in the art.

One embodiment of such a system is shown in FIG. 1. The system includes an inspection subsystem that includes at least an energy source and a detector. The energy source is configured to generate energy that is directed to a specimen. The detector is configured to detect energy from the specimen and to generate output responsive to the detected energy.

In one embodiment, the energy directed to the specimen includes light, and the energy detected from the specimen includes light. For example, in the embodiment of the system shown in FIG. 1, inspection subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the inspection subsystem may be configured to alter one or more characteristics of one or more elements of the illumination subsystem such that the light can be directed to the specimen at an angle of incidence that is different than that shown in FIG. 1. In one such example, the inspection subsystem may be configured to move light source 16, optical element 18, and lens 20 such that the light is directed to the specimen at a different angle of incidence.

In some instances, the inspection subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem may also include a scanning subsystem configured to cause the light to be scanned over the specimen. For example, the inspection subsystem may include stage 22 on which specimen 14 is disposed during inspection. The scanning subsystem may include any suitable mechanical and/or robotic assembly (that includes stage 22) that can be configured to move the specimen such that the light can be scanned over the specimen. In addition, or alternatively, the inspection subsystem may be configured such that one or more optical elements of the inspection subsystem perform some scanning of the light over the specimen. The light may be scanned over the specimen in any suitable fashion.

The inspection subsystem further includes one or more detection channels. At least one of the one or more detection channels includes a detector configured to detect light from the specimen due to illumination of the specimen by the inspection subsystem and to generate output responsive to the detected light. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the inspection subsystem that includes two detection channels, the inspection subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the output described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the system as is normally performed when designing a commercial inspection system. In addition, the systems described herein may be implemented using an existing inspection system (e.g., by adding functionality described herein to an existing inspection system) such as the 28xx and 29xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the inspection subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number of functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the inspection subsystem is described above as being an optical or light-based inspection subsystem, the inspection subsystem may be an electron beam-based inspection subsystem. For example, in one embodiment, the energy directed to the specimen includes electrons, and the energy detected from the specimen includes electrons. In this manner, the energy source may be an electron beam source. In one such embodiment shown in FIG. 2, the inspection subsystem includes electron column 122, which is coupled to computer subsystem 124.

Figure 2:
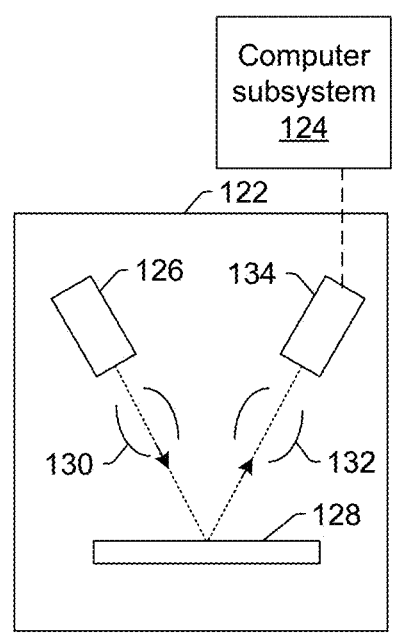

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based subsystem may be configured to use multiple modes to generate images of the specimen (e.g., with different illumination angles, collection angles, etc.). The multiple modes of the electron beam-based subsystem may be different in any image generation parameters of the subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the inspection subsystem shown in FIG. 2 may be further configured as described herein.

It is noted that FIG. 2 is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the eSxxx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Although the inspection subsystem is described above as being a light-based or electron beam-based inspection subsystem, the inspection subsystem may be an ion beam-based inspection subsystem. Such an inspection subsystem may be configured as shown in FIG. 2 except that the electron beam source may be replaced with any suitable ion beam source known in the art. In addition, the inspection subsystem may be any other suitable ion beam-based subsystem such as those included in commercially available focused ion beam (FIB) systems, helium ion microscopy (HIM) systems, and secondary ion mass spectroscopy (SIMS) systems.

The computer subsystem(s) are configured for identifying a first portion of dies on the specimen as edge dies based on positions of the dies on the specimen and identifying a second portion of the dies on the specimen as center dies based on the positions of the dies on the specimen. The center dies are located farther from an edge of the specimen than the edge dies. In this manner, the computer subsystem(s) may be configured for segregating defect detection jobs such that the edge dies are combined in one group and center dies into another group.

The computer subsystem(s) may identify the edge and center dies based on a die layout for the specimen, which may include positions of the dies on the specimen and therefore positions relative to a center and edge of the specimen. Therefore, the computer subsystem(s) can use the information about the die layout to determine how far each die is from an edge (and center) of the specimen. The computer subsystem(s) may also be configured for using the information about those distances to determine which dies are located adjacent to an edge of the specimen and/or closer to the edge than other dies. In addition, the computer subsystem(s) may be configured for using the information about those distances to determine which dies are located adjacent to a center of the specimen and/or closer to the center than other dies.

How close a die must be to an edge of a specimen to be considered an edge die and how close a die must be to a center of a specimen to be considered a center die may vary depending on process and/or noise characteristics of the specimen. For example, preferably, the dies that are identified by the computer subsystem(s) as edge dies are those that have higher levels of noise and defects due to process variations on the specimen while the dies that are identified by the computer subsystem(s) as center dies are those that have lower levels of noise and defects due to process variations on the specimen. Therefore, some information about the process and/or noise variations on the specimen may be used to determine how far a die must be from an edge and a center of the specimen to be considered an edge and center die, respectively. That information can be acquired in a number of different manners (e.g., from measuring the noise levels across another specimen that is the same type as the specimen that will be inspected, based on noise levels on other specimens processed with the same tools as the specimen (i.e., based on tool history), based on simulations or calculations of the noise levels across the specimen).

Figure 3:
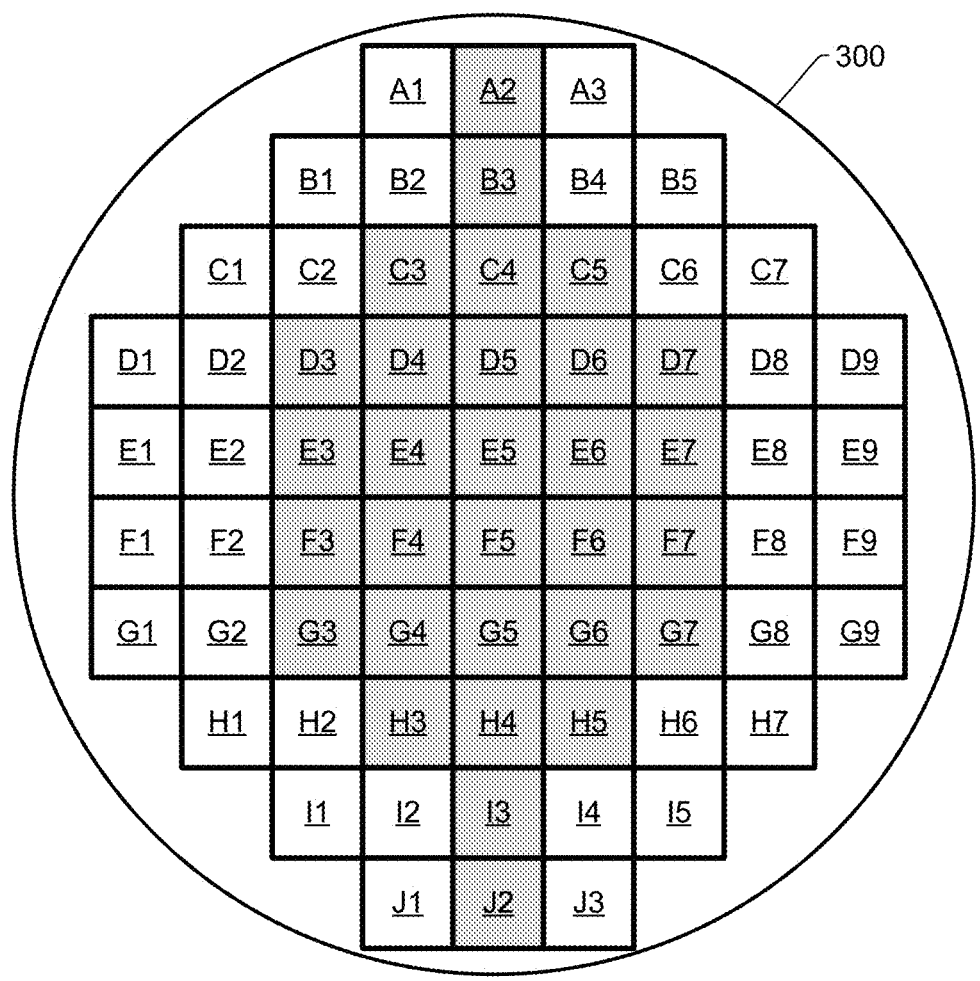
FIG. 3 is a schematic diagram illustrating a plan view of one embodiment of dies formed on a specimen.

In one such example, as shown in FIG. 3, wafer 300 may include a layout of dies that include at least some center dies and at least some edge dies. In this example, the center dies are shaded while the edge dies are not. For example, in the "E" row on the wafer, dies E1, E2, E8, and E9 are edge dies while dies E3-E7 are center dies. In another example, in the "A" row on the wafer, dies A1 and A3 are edge dies while die A2 is a center die. The edge dies and the center dies may be identified based on radial position in that dies that are located farthest from a center of the wafer along a radius of the wafer may be identified as edge dies while dies that are located closer to the center of the wafer along a radius of the wafer may be identified as center dies. The edge dies and center dies on wafer 300 may otherwise be identified as described further herein.

In one embodiment, identifying the first and second portions of the dies is further based on the positions of the dies on the specimen and noise characteristics of the dies. For example, the computer subsystem(s) may be configured for generating a noise distribution profile for each die row and for segregating the dies to be inspected for each die row based on the noise level. Dies with relatively low noise may be grouped together and inspected together, and dies with relatively high noise may be grouped and inspected separately. The noise characteristics of the dies used in this embodiment may be determined as described further herein (e.g., based on tool history, noise levels on another specimen, simulations of the noise levels on the specimen).

The computer subsystem(s) are also configured for determining a first inspection method for the first portion of the dies based on the positions of the edge dies on the specimen and a second inspection method for the second portion of the dies based on the positions of the center dies on the specimen. In this manner, different inspection methods may be performed by the embodiments described herein for edge dies and center dies. The inspection methods determined for the first and second portions of the dies may be different in any parameters of the inspection methods. In addition, parameters of the inspection methods determined for the first and second portions of the dies may be completely independent of each other. Determining the first and second inspection methods may include determining any parameters of the inspection methods such as the comparisons that are performed in the inspection methods and the defect detection parameters that are applied to results of the comparisons. Determining such parameters may be performed as described further herein.

One or more parameters of comparisons of the dies performed in the first inspection method are different than one or more parameters of comparisons of the dies performed in the second inspection method. In this manner, the embodiments described herein may be configured for die-to-die inspection. In addition, the comparisons may be configured as described further herein so that dies that have similar radial positions on the specimen (locations that are spaced from a center of the specimen by the same distance) are compared to each other. The comparisons performed for the first and second inspection methods may be determined as described further herein. In addition, the first and second inspection methods may be different in at least the one or more parameters of the comparisons that are performed in the first and second inspection methods and possibly also different in one or more other parameters of the first and second inspection methods (e.g., one or more defect detection parameters, one or more scanning parameters).

The one or more parameters of the comparisons that are different for the first and second inspection methods may include, as described further herein, the dies that are compared in the comparisons. Each of the comparisons will, however, generally include comparing one die to another die. Therefore, the comparisons of the first and second inspection methods will generally include die-to-die comparisons. The results of those comparisons may then include difference images (generated by subtracting one die image from another die image in the comparisons). The difference images may then be used for additional steps in the first and second inspection methods (e.g., application of one or more defect detection parameters such as a threshold to the difference images for defect detection), which may be performed as described further herein.

In general, the embodiments described herein are configured for determining and performing double detection type inspection methods. In these inspection methods, a die in which defects are being detected (commonly referred to as a test die) is compared to two other dies (commonly referred to as reference dies). In this manner, whether a defect is present in the test die or one of the reference dies can be determined based on the results of the two comparisons. In other words, if a defect is detected based on results of only one comparison, the defect can be determined to not be present in the test die (instead it is in the reference die used for that one comparison). In contrast, if a defect is detected based on results of both comparisons, the defect can be determined to be present in the test die (since the test die is common to both of the comparisons). Therefore, defects in the test die are determined as only those defects detected by both comparisons, hence the name double detection inspection.

Figure 4:
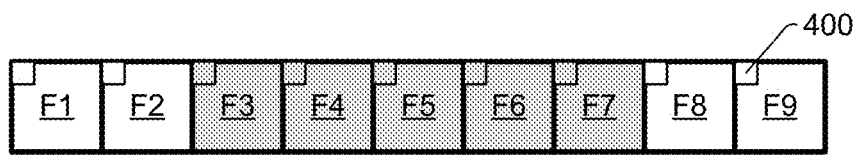
FIG. 4 is a schematic diagram illustrating a plan view of one die row on the specimen of FIG. 3 and corresponding job frames in each of the dies in the die row.
Figure 5:
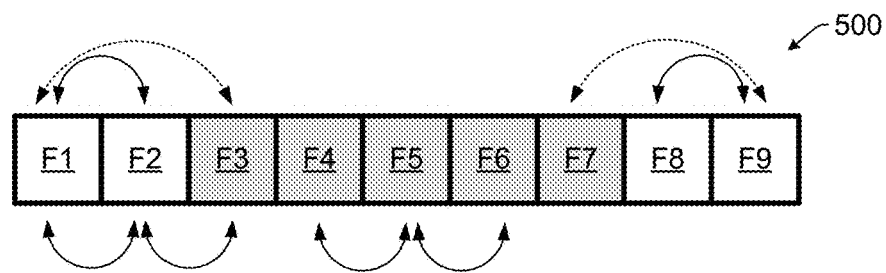
FIG. 5 is a schematic diagram illustrating a plan view of one die row on the specimen of FIG. 3 and previously used comparisons between dies in the die row performed for defect detection in the dies.

The embodiments described herein are therefore different from previously used methods and systems for die-to-die wafer inspection. For example, as shown in FIG. 4, each die in the "F" row on wafer 300 of FIG. 3 may include multiple frames, one of which is shown in each of the dies in FIG. 4 by frame 400. In previously used die-to-die inspection, the output of the detector of the inspection subsystem (e.g., a frame image) for one of frames 400 in one die is compared to one or more of the outputs generated for another of frames 400 in another die. For example, as shown in FIG. 5, for previously used inspection of die F1, image frames generated for die F1 may be compared to image frames generated for dies F2 and F3 at corresponding within die locations (as shown by the arrows above these dies in FIG. 5) in a double detection scheme. In another example shown in FIG. 5, for previously used inspection of die F2, image frames generated for die F2 may be compared to image frames generated for dies F1 and F3 at corresponding within die locations (as shown by the arrows below these dies in FIG. 5) in a double detection scheme. In a further example shown in FIG. 5, for previously used inspection of die F5, image frames generated for die F5 are compared to image frames generated for dies F4 and F6 at corresponding within die locations (as shown by the arrows below these dies in FIG. 5) in a double detection scheme. In still another example, as shown in FIG. 5, for previously used inspection of die F9, image frames generated for die F9 are compared to image frames generated for dies F7 and F8 at corresponding within die locations (as shown by the arrows above these dies in FIG. 5) in a double detection scheme. In this manner, in previously used die-to-die inspection methods, center dies and edge dies are compared against each other for die-to-die inspection. Therefore, since the edge and center dies may have substantially different noise characteristics, comparing an edge die to a center die can result in the detection of the differences in the noise characteristics as potential defects. As such, depending on the threshold that is applied to the detected differences, those differences in the noise characteristics can be detected as actual defects. Consequently, such inspection methods can detect a significant number of differences in noise characteristics as actual defects when in actuality they are simply nuisance defects (i.e., not actual defects on the specimen).

In one embodiment, the comparisons performed in the first inspection method do not include comparing the output generated for any of the edge dies with the output generated for any of the center dies, and the comparisons performed in the second inspection method do not include comparing the output generated for any of the center dies with the output generated for any of the edge dies. In other words, defect detection jobs performed by the embodiments described herein may include combining inner dies and edge dies separately. In other words, center dies are compared against each other for defect detection, and edge dies are compared with edge dies. Assuming noise levels are similar for edge dies and dissimilar between edge dies and center dies, segregating them in different buckets will advantageously improve defect detection quality. In this manner, the embodiments described herein advantageously improve the sensitivity of inspection of both edge dies and center dies using the techniques described further herein.

Figure 6:
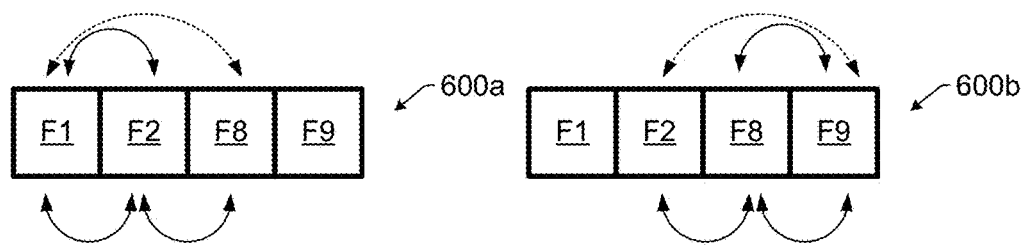
FIGS. 6-9 are schematic diagrams illustrating plan views of different portions of dies in die rows on the specimen of FIG. 3 and embodiments of different comparisons between dies performed in different inspection method embodiments described herein.
Figure 7:
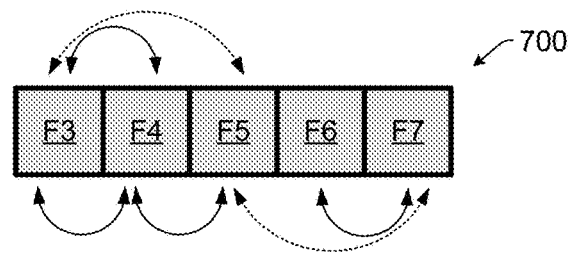

In one such example, as shown in FIG. 6, the edge dies in row "F" of wafer 300 shown in FIG. 3 can be segregated into one group, which does not include any of the center dies in row F of the specimen. In particular, edge dies F1, F2, F8, and F9 may be separated into one group that does not include any inner dies. Various comparisons can then be made among those dies to thereby detect defects in those dies. In this manner, the edge dies may be compared against each other. In contrast, for the same "F" row, center dies F3-F7 can be segregated into their own group, as shown in group 700 in FIG. 7. As shown in FIG. 7, this group does not include any of the edge dies in row "F." In this manner, the edge dies and the center dies may be separated into different groups that include only one type of dies (either edge dies or center dies). Various comparisons can then be made among those dies to thereby detect defects in those dies. In this manner, center dies can be compared against only each other.

In another embodiment, the comparisons performed in the first inspection method include a first comparison of the output generated for a first of the edge dies with the output generated for a second of the edge dies adjacent to the first edge die on the specimen and a second comparison of the output generated for the first edge die with the output generated for a third of the edge dies adjacent to the first edge die on the specimen. In this manner, if adjacent (edge) dies are available, they can be used for defect double detection algorithms and/or methods. For example, if enough edge dies needed for a comparison scheme are located in a die row and therefore will be scanned together, those edge dies can be compared against each other.

In an additional embodiment, the comparisons performed in the first inspection method include a first comparison of the output generated for a first of the edge dies with the output generated for a second of the edge dies adjacent to the first edge die on the specimen and a second comparison of the output generated for the first edge die with the output generated for a third of the edge dies spaced from the first edge die on the specimen. In this manner, if only one adjacent edge die is available for double defect detection in a candidate edge die image, that adjacent edge die can be used as a first reference and the second reference image may be acquired on the other side of the specimen, possibly with the same radial distance from the specimen center as the candidate image. In this manner, if the edge dies on one side of the specimen are not present in a number sufficient for double detection, edge dies from different sides (e.g., left and right edge dies) may be compared to each other for defect detection. For example, if enough edge dies needed for a comparison scheme are located in a die row and therefore will be scanned together, those edge dies can be compared against each other even if they are not all adjacent to one another on the specimen.

In one such example, as shown in instance 600a of FIG. 6, for die-to-die inspection of edge die F1, comparisons may be performed between edge die F1 and edge die F2 and between edge die F1 and edge die F8 as shown by the arrows above the dies in instance 600a. As shown in FIG. 3, edge dies F1 and F2 are located adjacent to each other on wafer 300 while edge dies F1 and F8 are spaced from each other on the wafer. In another such example, as also shown in instance 600a of FIG. 6, for die-to-die inspection of edge die F2, comparisons may be performed between edge die F2 and edge die F1 and between edge die F2 and edge die F8 as shown by the arrows located below the dies in instance 600a. As shown in FIG. 3, edge dies F2 and F1 are located adjacent to each other on wafer 300 while edge dies F2 and F8 are spaced from each other on the wafer. In the above-described comparison schemes, edge die F8 may be replaced with edge die F9 and the comparisons would yield similar advantages over the previously used comparisons for die-to-die inspection.

In a further such example, as shown in instance 600b of FIG. 6, for die-to-die inspection of edge die F9, comparisons may be performed between edge die F9 and edge die F8 and between edge die F9 and edge die F2, as shown by the arrows above the dies in instance 600b. As shown in FIG. 3, edge dies F9 and F8 are located adjacent to each other on wafer 300 while edge dies F9 and F2 are spaced from each other on the wafer. In still another example, as also shown in instance 600b of FIG. 6, for die-to-die inspection of edge die F8, comparisons may be performed between edge die F8 and edge die F9 and between edge die F8 and edge die F2, as shown by the arrows below the dies shown in instance 600b. As shown in FIG. 3, edge dies F8 and F9 are located adjacent to each other on wafer 300 while edge dies F8 and F2 are spaced from each other on the wafer. In the above-described comparison schemes, edge die F2 may be replaced with edge die F1, and the comparisons would yield similar advantages over the previously used comparisons performed for die-to-die inspection.

In a further embodiment, the comparisons performed in the first inspection method include a first comparison of the output generated for a first of the edge dies with the output generated for a second of the edge dies spaced from the first edge die on the specimen and a second comparison of the output generated for the first edge die with the output generated for one of the center dies on the specimen. For example, for detection in an edge die, if an adjacent edge die is not available as a first reference, an edge die from a diametrical opposite side (or otherwise spaced from the edge die in which defects are being detected) is used. In such a scenario, if a second reference edge die is not available, a center die may be used as the second reference. In another example, for detection in an edge die, an outermost die on one side of the specimen may always be used as a reference for an outermost die on the other side of the specimen. In this scenario, if a second reference edge die is not available, an adjacent center die may be used as the second reference. In this manner, if the number of the edge dies for a given row is less than three, the edge dies in that row can be compared to each other and for arbitration a reference die can be used, which could be an image frame from a center die. As such, when the edge dies in a given die row are not sufficient, a reference die may be taken from a center die.

The purpose of the non-edge reference die is to allow the determination of the die that has the highest defect signal, which can then be identified as containing a defect. In this manner, unlike instance in which the references dies are both edge dies, when using a non-edge die for arbitration, the non-edge die reference may be compared against the other two edge dies, the test edge die and the reference edge die. This is unlike double detection using three edge dies in which the reference edge dies are not compared to each other. The differences between the two edge dies and the non-edge reference die can then be used to determine which of the two edge dies has the highest signal. If the difference between the test edge die and the non-edge die reference is higher than the difference between the reference edge die and the non-edge die reference, then the defect is determined to be in the test edge die. If the difference between the reference edge die and the non-edge die reference is higher than the difference between the test edge die and the non-edge die reference, then the defect is not determined to be in the test die image. In such instances, a defect may be identified in the reference edge die. In this manner, in inspection methods in which one of the reference dies is a non-edge die, instead of double detection type comparisons, the comparisons may be performed for a type of inspection that can be described as single detection followed by arbitration.

Figure 8:
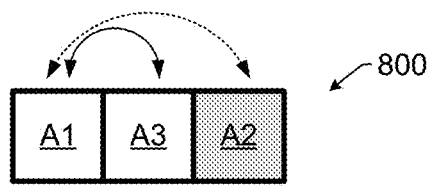

One such example in which there are not enough edge dies in a die row for edge die-to-edge die comparisons in a double detection scheme is shown in FIG. 3 in die row "A." In particular, as shown in FIG. 3, die row "A" includes two edge dies A1 and A3 and one center die A2. Therefore, die row "A" does not include enough edge dies needed for a die-to-die double detection scheme, i.e., 3 edge dies. One solution for inspecting the edge dies in this die row is therefore to compare the edge dies against each other and to use the center die as a reference. For example, as shown in FIG. 8, in comparison scheme 800 for inspection of edge die A1, edge die A1 is compared to edge die A3 and edge die A1 is also compared to center die A2, as shown by the arrows above the dies in FIG. 8. The results of these comparisons can be used as described further herein to detect defects in edge die A1. In a similar manner, for inspection of edge die A3, edge die A3 may be compared to edge die A1 and edge die A3 may also be compared to center die A2. The results of these comparisons can also be used as described further herein to detect defects in edge die A3.

In another embodiment, the comparisons performed in the first inspection method include a first comparison of the output generated for a first of the edge dies with the output generated for a second of the edge dies spaced from the first edge die on the specimen and a second comparison of the output generated for the first edge die with a design rendered image of the dies. For example, for detection in an edge die, if an adjacent edge die is not available as a first reference, an edge die from a diametrical opposite side (or an edge die otherwise spaced from the test edge die) is used. In such a scenario, if a second reference edge die is not available, a design rendered image may be used as the second reference image. In another example, for detection in an edge die, an outermost die on one side of the specimen may always be used as a reference for an outermost die on the other side of the specimen. In this scenario, if a second reference edge die is not available, a design rendered image may be used as the second reference. In this manner, if the number of the edge dies for a given row is less than three, the edge dies in that row can be compared to each other and for arbitration a reference die will be used, which could be an image from a rendered design of the corresponding image frame. As such, when the edge dies in a given die row are not sufficient, a reference die may be taken from a rendered design. The purpose of the reference die is to allow the determination of the die that has the highest defect signal, which can then be identified as containing a defect. Arbitration using a non-edge reference die may be performed in these embodiments as described further herein.

The reference die used in any of the comparisons described herein may be generated and further configured as described herein with respect to a single reference die used for alignment. In other words, the reference die used in any of the comparisons described herein may be generated by performing one or more of the simulations described further herein. In addition, the simulations may or may not take into account the noise characteristics of the die(s) that the rendered image(s) will be compared to. For instance, if the simulations do not take into account the process variations (e.g., process noise on and near edges of the specimen), then the design rendered image may appear substantially similar to an image of one of the center dies rather than one of the edge dies. In this manner, the design rendered image may be used for defect arbitration as described further herein. However, in some instances, if the simulation is able to model the process noise on the edges of the specimen, then the design rendered image may appear substantially similar to an image of the edge dies. In this manner, the design rendered image may be used as an edge die equivalent in the double detection schemes described further herein (i.e., as a simulated reference edge die image).

Figure 9:
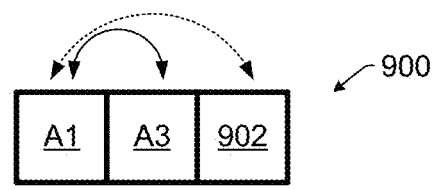

One such example in which there are not enough edge dies in a die row for edge die-to-edge die comparisons in a double detection scheme is shown in FIG. 3 in die row "A." In particular, as shown in FIG. 3, die row "A" includes two edge dies A1 and A3 and one center die A2. Therefore, die row "A" does not include enough edge dies needed for a die-to-die double detection scheme, i.e., 3 edge dies. One solution for inspecting the edge dies in this die row is therefore to compare the edge dies against each other and to use a design rendered frame as a reference. For example, as shown in FIG. 9, in comparison scheme 900 for inspection of edge die A1, edge die A1 is compared to edge die A3 and edge die A1 is also compared to design rendered image 902, which may be generated and configured as described herein, as shown by the arrows above the dies in FIG. 9. The results of these comparisons can be used as described further herein to detect defects in edge die A1, which may include defect arbitration as described further herein. In a similar manner, for inspection of edge die A3, edge die A3 may be compared to edge die A1 and edge die A3 is also compared to design rendered image 902, which may be generated and configured as described herein. The results of these comparisons can be used as described further herein to detect defects in edge die A3, which may include defect arbitration described further herein.

In still another embodiment, the comparisons performed in the second inspection method include a first comparison of the output generated for a first of the center dies with the output generated for a second of the center dies adjacent to the first center die on the specimen and a second comparison of the output generated for the first center die with the output generated for a third of the center dies adjacent to the first center die on the specimen. In this manner, for center dies on the specimen, adjacent center dies may be used as reference images for a candidate center die image.

In one such example, as shown in FIG. 7, in die-to-die inspection of the center dies in row "F" of wafer 300 shown in FIG. 3, for inspection of center die F3, comparisons may be performed between center die F3 and center die F4 and between center die F3 and center die F5 as shown by the arrows above these dies in FIG. 7. In a similar manner, as shown in FIG. 7, for inspection of center die F4, comparisons may be performed between center die F4 and center die F3 and between center die F4 and center die F5 as shown by the arrows below these dies in FIG. 7. In another example, for inspection of center die F7, comparisons may be performed between center die F7 and center die F6 and between center die F7 and center die F5 as shown by the arrows below these dies in FIG. 7. Similar comparisons can be performed for inspection of center dies F5 and F6. The results of all of these comparisons may be used as described further herein for defect detection, which may be performed as described further herein. In this manner, for inspection of center dies, output of the detector, e.g., images, generated for only center dies may be compared to each other. In other words, for inspection of center dies, the output generated by the detector for a center die may not be compared to the output generated for an edge die.

In another example, for double defect detection in a center die, a center die having a position along a radius of the specimen that is the same as the position along a radius of the specimen of another center die may always be used as a reference for the other center die. In this manner, two center dies that are spaced from a center of the specimen by the same distance may be compared for one comparison of a double detection method and/or algorithm. In one such scenario, if a second center die is not available, an adjacent edge die may be used as the second reference. In another such scenario, if a reference edge die is not available for double detection in such a center die, a design rendered image may be used as the second reference. In these cases, the purpose of the reference die is to allow the determination of the die that has highest defect signal, which can then be identified as containing a defect. The design rendered image may include any of the design rendered images described herein and may be generated and configured as described herein. In addition, the arbitration using the design rendered image or other non-center reference die may be performed as described further herein.

In some embodiments, the inspection subsystem includes a scanning subsystem configured to scan the energy directed to the specimen over the specimen as the detector detects the energy from the specimen, and the one or more computer subsystems are configured for determining a first scanning strategy performed by the scanning subsystem in the first inspection method and a second scanning strategy performed by the scanning subsystem in the second inspection method. The scanning subsystem may be configured as described and shown with respect to FIG. 1. The first and second scanning strategies may be different than each other and may depend on the dies that are to be compared in the first and second inspection methods. For example, the swathing strategy may be modified such that inner (or center) dies are compared against each other and similar edge dies are compared against other edge dies.

In one such example, the dies that are to be compared in the first inspection method may be scanned one after the other in a sequence even if the dies are not located adjacent to each other on the specimen. In this manner, the adjacent dies on the specimen may not necessarily be scanned one after the other, e.g., if the adjacent dies are not to be compared to each other. The computer subsystem(s) may therefore determine the scanning strategies such that dies that are to be compared to each other are scanned in a sequence without also scanning other dies. The computer subsystem(s) may also determine the scanning strategies in this manner based on any of the other information described herein (e.g., which dies are center dies, which dies are edge dies, the die layout and positions on the specimen, etc.). The computer subsystem(s) may then control the scanning subsystem of the inspection subsystem in any suitable manner (e.g., by sending instructions for the different scanning strategies to the inspection subsystem and/or the scanning subsystem and/or a control subsystem (not shown) coupled to the inspection subsystem and/or the scanning subsystem) such that the scanning subsystem can cause the dies to be scanned according to the scanning strategies. In this manner, the length of time that the output of the detector is stored in the computer subsystem(s) or storage media coupled thereto until the comparisons can be performed can be minimized.

As described above, the swathing strategy used for any of the inspection methods may be altered depending on which of the dies are being compared in the inspection methods (e.g., so that the dies that will be compared are scanned as though they are adjacent dies on the specimen). However, in some embodiments, the computer subsystem(s) described herein may be configured to store relatively large amounts of output of the detector such as images (e.g., an entire swath of output or images or all of the output or images generated for an entire specimen during an inspection process). Therefore, the computer subsystem(s) may have access to any image generated at any point in a die row for a comparison performed in an inspection method regardless of how the specimen was scanned. One embodiment of such a computer subsystem includes one or more computer subsystem(s) configured as a virtual inspector.

In one such embodiment, the one or more computer subsystems include at least one virtual inspection system also commonly referred to as a virtual inspector (VI). A VI can be generally defined as a computer system that can store massive amounts of output generated for a wafer by an inspection subsystem such that the output can be "played back" in a manner that mimics real time acquisition of the output during which a virtual inspection can be performed for the wafer using only the stored output. Examples of such virtual inspectors are illustrated in U.S. Pat. No. 8,126,255 issued on Feb. 28, 2012 to Bhaskar et al. and U.S. Pat. No. 9,222,895 issued on Dec. 29, 2015 to Duffy et al., which are incorporated by reference as if fully set forth herein. The computer subsystem(s) described herein may be further configured as described in these patents.

In the embodiments described herein, a VI may be particularly useful for performing one or more offline steps during setup and/or for storage of the various information and/or images generated and/or used in the embodiments described herein. For example, a VI may be particularly useful for setup of the die-to-die inspection described herein. In one such example, a VI may be configured for extracting design clips (i.e., relatively small portions of an entire design of a die on a wafer) from a design database (DB) or file. In addition, a VI may be configured for generating the rendered reference images described herein and storing the rendered reference images.

A VI may also be configured for performing one or more of the steps described herein online. For example, a VI may be configured to perform the die-to-die inspection (i.e., the image compare and defect detection steps described herein) online (and offline as well). Furthermore, since a VI may include multiple image computer nodes, performance of any of the steps described herein can be distributed across the multiple image computer nodes thereby providing advantages for throughput.

In one embodiment, the first inspection method includes applying one or more first defect detection parameters to results of the comparisons performed in the first inspection method, and the second inspection method includes applying one or more second defect detection parameters to results of the comparisons performed in the second inspection method. For example, the comparisons described herein will produce results such as difference images (e.g., the differences between various detector outputs such as images depending on which dies or references are compared). One or more defect detection parameters may then be applied to the difference images or other results of the comparisons to determine if differences in the results are defects or correspond to defects. In one such example, the one or more parameters include at least one threshold. If the differences in the results of the comparisons are greater than the threshold, then the differences may be determined to be defects. In contrast, if the differences in the results of the comparisons are lower than the threshold, then the differences may not be determined to be defects. Detecting the defects on the specimen may be performed in this or any other suitable manner known in the art with any suitable defect detection method and/or algorithm. The one or more defect detection parameters may include any parameters used for defect detection, including those that relate to the sensitivity of the defect detection (e.g., a threshold) and those used for arbitration or any other steps performed in the defect detection method and/or algorithm.

In one such embodiment, the one or more first defect detection parameters are independent of the one or more second defect detection parameters. For example, whether or not the first and second defect detection parameters are the same or different, the one or more first defect detection parameters may be determined separately from and independent of the one or more second defect detection parameters. In this manner, the one or more first defect detection parameters may be different than the one or more second defect detection parameters. However, the one or more first defect detection parameters and the one or more second defect detection parameters may not necessarily be different. For instance, due to the comparisons described herein that may be performed for defect detection in edge dies, the defect detection parameters used for detecting defects based on results of those comparisons may be just as sensitive as the defect detection parameters that are used for defect detection in center dies on the wafer. Therefore, the embodiments described herein may be different than previously used methods and systems in that the sensitivity of the inspection performed for edge dies does not have to be reduced in order to control the number or amount of defects detected in the edge dies, which has previously been substantially high due to the noise and process variations present in these edge dies. Instead, the embodiments described herein account for these noise and process variations in the edge dies in the comparison steps thereby allowing the defect detection to be more sensitive in the edge dies.

In another such embodiment, the one or more first defect detection parameters and the one or more second defect detection parameters are selected by a user. For example, the user may be provided with the opportunity to tune the defect detection parameters separately for edge die inspection and center die inspection. In one such example, the computer subsystem(s) may display a user interface (UI) that can be used by a user to input the first defect detection parameter(s) separately from the second defect detection parameter(s). The computer subsystem(s) may also perform other steps related to receiving such input from a user such as requesting the input, storing the input, modifying program instructions (i.e., a recipe) for the inspection methods based on the input, performing the inspection methods based on the input, etc. In this manner, the user can control the level of defectivity that is detected and reported in the edge dies and the center dies separately. Enabling such user control of the defect detection parameters may be advantageous for the user since the user may care more about the defectivity of center dies than the edge dies or vice versa.

In some embodiments, the one or more computer subsystems are configured for aligning the output generated in each die row on the specimen with a single reference die. In this manner, for each die row, run time alignment (RTA) may be performed with respect to a single reference die, which is different than the current mechanism for RTA that includes performing adjacent die alignment. In this manner, the embodiments described herein may be configured for reference die based RTA. Aligning the output to the single reference die may be performed in a number of different manners. For example, the output may be aligned to the single reference die by pattern matching or any other suitable aligning method and/or algorithm known in the art. The output that is aligned to the single reference die may include any of the output of the detector (e.g., images) described herein. In addition, the single reference die may include different types of information such as the design data itself or other types of design information described herein.

The single reference die may be one of the center dies on the specimen or a first die scanned on the specimen. In another embodiment, the computer subsystem(s) are configured for generating a simulated image illustrating how one or more of the dies will appear in the output generated by the detector and aligning the output generated in each die row on the specimen with the simulated image. In some such embodiments, the computer subsystem(s) may be configured for learning image rendering parameters from example reference die(s). Learning the image rendering parameters may be performed in any suitable manner (e.g., as in setting up and/or calibrating a simulation model or method). The example reference die(s) may include suitable dies that have been actually imaged by the inspection subsystem. In addition, the example reference die(s) may include a selection of representative die(s) that include various patterns, e.g., dense geometry, sparse geometry, etc. To generate the most accurate simulated images, the simulation can involve the simulation of electromagnetic (EM) field by solving Maxwell's equations from three-dimensional information for the chip design and material, followed by simulation of the optical parameters of the inspection subsystem used to form an image of the specimen.

The computer subsystem(s) may also be configured for determining one or more offsets between the output and the example reference die(s) based on results of the aligning. In this manner, the computer subsystem(s) described herein may be configured to determine reference die-to-output offsets. The computer subsystem(s) may also be configured for saving information for the single reference die and the determined offset(s) to a computer-readable storage medium such as a database or one of the other storage media described herein for run time inspection.

The reference die-to-output offsets may be determined in any suitable manner based on one or more portions of the single reference die that match the output and their corresponding reference die coordinates and inspection space (e.g., inspection subsystem or specimen) coordinates, respectively. The reference die-to-output offsets may have any suitable format (e.g., a function or formula). In addition, information for the reference die-to-output offsets may be stored in any suitable storage media described herein. Furthermore, the reference die-to-output offsets may be determined in one only direction (e.g., the x or the y direction) or in two directions (e.g., the x and y directions). Moreover, the reference die-to-output offsets may be determined using design data space and inspection space coordinates having any suitable format (e.g., polar and Cartesian coordinates).

In one embodiment, determining the one or more offsets is performed for each inspection frame of the output generated by the inspection subsystem for the specimen. For example, the computer subsystem(s) may be configured to determine reference die-to-output offsets for each inspection frame from the single reference die. An inspection "frame" or "job" may be generally defined as a relatively small portion of output generated by an inspection subsystem that can be collectively processed as a unit by the system.

Therefore, a "frame" of output can vary depending on the inspection subsystem configuration as well as the configuration of any components included in the system for handling and/or processing the output generated by the inspection subsystem. In this manner, the embodiments described herein may be configured for job level based RTA.

The computer subsystem(s) are further configured for detecting defects in at least one of the edge dies by performing the first inspection method for the at least one edge die in the first portion. Performing the first inspection method includes performing the comparisons in the first inspection method with the output of the detector for the at least one edge die. Performing the first inspection method may also include performing any of the other steps for the first inspection method described herein (e.g., defect arbitration based on results of the comparisons, defect detection based on results of the comparisons, etc.). All of these steps may be further performed as described herein.

The computer subsystem(s) are also configured for detecting defects in at least one of the center dies by performing the second inspection method for the at least one center die in the second portion. Performing the second inspection method includes performing the comparisons in the second inspection method with the output of the detector for the at least one center die. Performing the second inspection method may also include performing any of the other steps for the second inspection method described herein (e.g., defect arbitration based on results of the comparisons, defect detection based on results of the comparisons, etc.). All of these steps may be further performed as described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

In one such example, the results of detecting the defects in the at least one edge die and the at least one center die may be combined into a single set of inspection results for the wafer. In other words, although the embodiments described herein include setting up and performing different inspection methods for edge dies compared to center dies, the different inspection methods may be performed in a single inspection process for the specimen. In this manner, the results of each of the different inspection methods that is performed for the specimen may be combined into a single set of inspection results for the specimen. The single set of inspection results generated for the specimen by the computer subsystem(s) may have any suitable format known in the art and may include as much or as little information as the user wants (e.g., defect ID, defect location, etc.). The inspection results may be stored and/or used in any suitable manner (e.g., for dispositioning the specimen and/or the process(es) performed on the specimen).

Another embodiment relates to a computer-implemented method for detecting defects on a specimen. The method includes steps for each of the functions of the computer subsystem(s) described above. The inspection subsystem is configured as described herein.

Each of the steps of the method may be performed as described further herein. The method may also include any other step(s) that can be performed by the inspection subsystem and/or computer subsystem(s) or system(s) described herein. The steps of the method are performed by one or more computer systems, which may be configured according to any of the embodiments described herein. In addition, the method described above may be performed by any of the system embodiments described herein.

Figure 10:
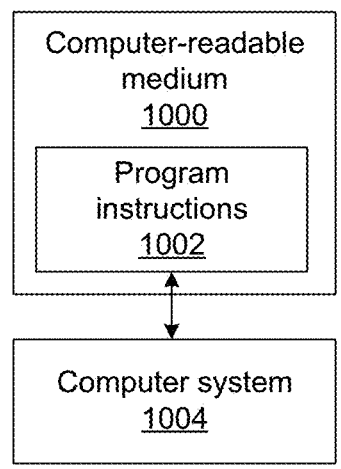
FIG. 10 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for detecting defects on a specimen. One such embodiment is shown in FIG. 10. In particular, as shown in FIG. 10, non-transitory computer-readable medium 1000 includes program instructions 1002 executable on computer system 1004. The computer-implemented method may include any step(s) of any method(s) described herein.

Program instructions 1002 implementing methods such as those described herein may be stored on computer-readable medium 1000. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 1004 may be configured according to any of the embodiments described herein.

Further modifications and alternative embodiments of various aspects of the invention will be apparent to those skilled in the art in view of this description. For example, methods and systems for detecting defects on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a specimen, comprising:
   an inspection subsystem comprising at least an energy source and a detector, wherein the energy source is configured to generate energy that is directed to a specimen, and wherein the detector is configured to detect energy from the specimen and to generate output responsive to the detected energy; and
   one or more computer subsystems configured for:
   identifying a first portion of dies on the specimen as edge dies based on positions of the dies on the specimen;
   identifying a second portion of the dies on the specimen as center dies based on the positions of the dies on the specimen, wherein the center dies are located farther from an edge of the specimen than the edge dies;

determining a first inspection method for the first portion of the dies based on the positions of the edge dies on the specimen and a second inspection method for the second portion of the dies based on the positions of the center dies on the specimen, wherein one or more parameters of comparisons of the dies performed in the first inspection method are different than one or more parameters of comparisons of the dies performed in the second inspection method;

wherein the inspection subsystem generates the output for at least one of the edge dies and at least one of the center dies by directing the energy from the energy source to the specimen and detecting the energy from the specimen with the detector;

detecting defects in the at least one of the edge dies by performing the first inspection method for the at least one edge die in the first portion, wherein performing the first inspection method comprises performing the comparisons in the first inspection method with the output of the detector for the at least one edge die, and wherein the comparisons performed in the first inspection method comprise a first comparison of the output generated for a first of the edge dies with the output generated for a second of the edge dies adjacent to the first edge die on the specimen and a second comparison of the output generated for the first edge die with the output generated for a third of the edge dies adjacent to the first edge die on the specimen, and detecting defects in the at least one of the center dies by performing the second inspection method for the at least one center die in the second portion, wherein performing the second inspection method comprises performing the comparisons in the second inspection method with the output of the detector for the at least one center die.

2. The system of claim 1, wherein said identifying the first and second portions of the dies is further based on the positions of the dies on the specimen and noise characteristics of the dies.

3. The system of claim 1, wherein the comparisons performed in the first inspection method do not include comparing the output generated for any of the edge dies with the output generated for any of the center dies, and wherein the comparisons performed in the second inspection method do not include comparing the output generated for any of the center dies with the output generated for any of the edge dies.

4. The system of claim 1, wherein the one or more computer subsystems are further configured for aligning the output generated in each die row on the specimen with a single reference die.

5. The system of claim 1, wherein the one or more computer subsystems are further configured for generating a simulated image illustrating how one or more of the dies will appear in the output generated by the detector and aligning the output generated in each die row on the specimen with the simulated image.

6. The system of claim 1, wherein the comparisons performed in the first inspection method further comprise third comparison of the output generated for the first edge die with the output generated for a fourth of the edge dies spaced from the first edge die on the specimen.

7. The system of claim 1, wherein the comparisons performed in the first inspection method further comprise a third comparison of the output generated for the first of the edge dies with the output generated for a fourth of the edge dies spaced from the first edge die on the specimen and a fourth comparison of the output generated for the first edge die with the output generated for one of the center dies on the specimen.

8. The system of claim 1, wherein the comparisons performed in the first inspection method further comprise a third comparison of the output generated for the first of the edge dies with the output generated for a fourth of the edge dies spaced from the first edge die on the specimen and a fourth comparison of the output generated for the first edge die with a design rendered image of the dies.

9. The system of claim 1, wherein the comparisons performed in the second inspection method comprise a first comparison of the output generated for a first of the center dies with the output generated for a second of the center dies adjacent to the first center die on the specimen and a second comparison of the output generated for the first center die with the output generated for a third of the center dies adjacent to the first center die on the specimen.

10. The system of claim 1, wherein the inspection subsystem further comprises a scanning subsystem configured to scan the energy directed to the specimen over the specimen as the detector detects the energy from the specimen, and wherein the one or more computer subsystems are further configured for determining a first scanning strategy performed by the scanning subsystem in the first inspection method and a second scanning strategy performed by the scanning subsystem in the second inspection method.

11. The system of claim 1, wherein the first inspection method comprises applying one or more first defect detection parameters to results of the comparisons performed in the first inspection method, and wherein the second inspection method comprises applying one or more second defect detection parameters to results of the comparisons performed in the second inspection method.

12. The system of claim 11, wherein the one or more first defect detection parameters are independent of the one or more second defect detection parameters.

13. The system of claim 11, wherein the one or more first defect detection parameters and the one or more second defect detection parameters are selected by a user.

14. The system of claim 1, wherein the specimen comprises a wafer.

15. The system of claim 1, wherein the energy directed to the specimen comprises light, and wherein the energy detected from the specimen comprises light.

16. The system of claim 1, wherein the energy directed to the specimen comprises electrons, and wherein the energy detected from the specimen comprises electrons.

17. A non-transitory computer-readable medium, storing program instructions executable on a computer system for performing a computer-implemented method for detecting defects on a specimen, wherein the computer-implemented method comprises:

identifying a first portion of dies on a specimen as edge dies based on positions of the dies on the specimen;

identifying a second portion of the dies on the specimen as center dies based on the positions of the dies on the specimen, wherein the center dies are located farther from an edge of the specimen than the edge dies;

determining a first inspection method for the first portion of the dies based on the positions of the edge dies on the specimen and a second inspection method for the second portion of the dies based on the positions of the center dies on the specimen, wherein one or more parameters of comparisons of the dies performed in the first inspection method are different than one or more parameters of comparisons of the dies performed in the second inspection method;

generating output for at least one of the edge dies and at least one of the center dies with an inspection subsystem, wherein the inspection subsystem comprises at least an energy source and a detector, wherein the energy source is configured to generate energy that is directed to the specimen, wherein the detector is configured to detect energy from the specimen and to generate the output responsive to the detected energy, and wherein generating the output with the inspection subsystem comprises directing the energy from the energy source to the specimen and detecting the energy from the specimen with the detector;

detecting defects in the at least one of the edge dies by performing the first inspection method for the at least one edge die in the first portion, wherein performing the first inspection method comprises performing the comparisons in the first inspection method with the output of the detector of the inspection subsystem for the at least one edge die, and wherein the comparisons performed in the first inspection method comprise a first comparison of the output generated for a first of the edge dies with the output generated for a second of the edge dies adjacent to the first edge die on the specimen and a second comparison of the output generated for the first edge die with the output generated for a third of the edge dies adjacent to the first edge die on the specimen; and detecting defects in the at least one of the center dies by performing the second inspection method for the at least one center die in the second portion, wherein performing the second inspection method comprises performing the comparisons in the second inspection method with the output of the detector for the at least one center die.

18. A computer-implemented method for detecting defects on a specimen, comprising:

identifying a first portion of dies on a specimen as edge dies based on positions of the dies on the specimen;

identifying a second portion of the dies on the specimen as center dies based on the positions of the dies on the specimen, wherein the center dies are located farther from an edge of the specimen than the edge dies;

determining a first inspection method for the first portion of the dies based on the positions of the edge dies on the specimen and a second inspection method for the second portion of the dies based on the positions of the center dies on the specimen, wherein one or more parameters of comparisons of the dies performed in the first inspection method are different than one or more parameters of comparisons of the dies performed in the second inspection method;

generating output for at least one of the edge dies and at least one of the center dies with an inspection subsystem, wherein the inspection subsystem comprises at least an energy source and a detector, wherein the energy source is configured to generate energy that is directed to the specimen, wherein the detector is configured to detect energy from the specimen and to generate the output responsive to the detected energy, and wherein generating the output with the inspection subsystem comprises directing the energy from the energy source to the specimen and detecting the energy from the specimen with the detector;

detecting defects in the at least one of the edge dies by performing the first inspection method for the at least one edge die in the first portion, wherein performing the first inspection method comprises performing the comparisons in the first inspection method with the output of the detector of the inspection subsystem for the at least one edge die, and wherein the comparisons performed in the first inspection method comprise a first comparison of the output generated for a first of the edge dies with the output generated for a second of the edge dies adjacent to the first edge die on the specimen and a second comparison of the output generated for the first edge die with the output generated for a third of the edge dies adjacent to the first edge die on the specimen; and detecting defects in the at least one of the center dies by performing the second inspection method for the at least one center die in the second portion, wherein performing the second inspection method comprises performing the comparisons in the second inspection method with the output of the detector for the at least one center die, and wherein identifying the first portion, identifying the second portion, determining the first and second inspection methods, detecting defects in the at least one edge die, and detecting defects in the at least one center die are performed by one or more computer subsystems coupled to the inspection subsystem.

19. A system configured to detect defects on a specimen, comprising:

an inspection subsystem comprising at least an energy source and a detector, wherein the energy source is configured to generate energy that is directed to a specimen, and wherein the detector is configured to detect energy from the specimen and to generate output responsive to the detected energy; and one or more computer subsystems configured for:

identifying a first portion of dies on the specimen as edge dies based on positions of the dies on the specimen;

identifying a second portion of the dies on the specimen as center dies based on the positions of the dies on the specimen, wherein the center dies are located farther from an edge of the specimen than the edge dies;

determining a first inspection method for the first portion of the dies based on the positions of the edge dies on the specimen and a second inspection method for the second portion of the dies based on the positions of the center dies on the specimen, wherein one or more parameters of comparisons of the dies performed in the first inspection method are different than one or more parameters of comparisons of the dies performed in the second inspection method;

wherein the inspection subsystem generates the output for at least one of the edge dies and at least one of the center dies by directing the energy from the energy source to the specimen and detecting the energy from the specimen with the detector;

detecting defects in the at least one of the edge dies by performing the first inspection method for the at least one edge die in the first portion, wherein performing the first inspection method comprises performing the comparisons in the first inspection method with the output of the detector for the at least one edge die, and wherein the comparisons performed in the first inspection method comprise a first comparison of the output generated for a first of the edge dies with the output generated for a second of the edge dies adjacent to the first edge die on the specimen and a second comparison of the output generated for the first edge die with the output generated for a third of the edge dies spaced from the first edge die on the specimen; and detecting defects in the at least one of the center dies by performing the second inspection method for the at least one center die in the second portion, wherein performing the second inspection method comprises performing the comparisons in the second inspection method with the output of the detector for the at least one center die.

20. A system configured to detect defects on a specimen, comprising:

an inspection subsystem comprising at least an energy source and a detector, wherein the energy source is configured to generate energy that is directed to a specimen, and wherein the detector is configured to detect energy from the specimen and to generate output responsive to the detected energy; and one or more computer subsystems configured for:

identifying a first portion of dies on the specimen as edge dies based on positions of the dies on the specimen;

identifying a second portion of the dies on the specimen as center dies based on the positions of the dies on the specimen, wherein the center dies are located farther from an edge of the specimen than the edge dies;

determining a first inspection method for the first portion of the dies based on the positions of the edge dies on the specimen and a second inspection method for the second portion of the dies based on the positions of the center dies on the specimen, wherein one or more parameters of comparisons of the dies performed in the first inspection method are different than one or more parameters of comparisons of the dies performed in the second inspection method;

wherein the inspection subsystem generates the output for at least one of the edge dies and at least one of the center dies by directing the energy from the energy source to the specimen and detecting the energy from the specimen with the detector;

detecting defects in the at least one of the edge dies by performing the first inspection method for the at least one edge die in the first portion, wherein performing the first inspection method comprises performing the comparisons in the first inspection method with the output of the detector for the at least one edge die; and detecting defects in the at least one of the center dies by performing the second inspection method for the at least one center die in the second portion, wherein performing the second inspection method comprises performing the comparisons in the second inspection method with the output of the detector for the at least one center die, and wherein the comparisons performed in the second inspection method comprise a first comparison of the output generated for a first of the center dies with the output generated for a second of the center dies adjacent to the first center die on the specimen and a second comparison of the output generated for the first center die with the output generated for a third of the center dies adjacent to the first center die on the specimen.

* * * * *